(12) United States Patent
Reichow et al.

(10) Patent No.: US 10,155,148 B2
(45) Date of Patent: Dec. 18, 2018

(54) VISION AND COGNITION TESTING AND/OR TRAINING UNDER STRESS CONDITIONS

(71) Applicant: NIKE, Inc., Beaverton, OR (US)

(72) Inventors: Alan W. Reichow, Beaverton, OR (US); Herb Yoo, Beaverton, OR (US)

(73) Assignee: NIKE, Inc., Beaverton, OR (US)

( * ) Notice: Subject to any disclaimer, the term of this patent is extended or adjusted under 35 U.S.C. 154(b) by 3 days.

(21) Appl. No.: 15/389,516

(22) Filed: Dec. 23, 2016

(65) Prior Publication Data

US 2017/0103666 A1    Apr. 13, 2017

Related U.S. Application Data

(62) Division of application No. 12/117,315, filed on May 8, 2008, now Pat. No. 9,564,058.

(51) Int. Cl.
*A63B 71/06* (2006.01)
*A61B 5/16* (2006.01)
(Continued)

(52) U.S. Cl.
CPC ............ *A63B 71/0622* (2013.01); *A61B 5/16* (2013.01); *A63B 21/06* (2013.01); *A63B 22/02* (2013.01);
(Continued)

(58) Field of Classification Search
CPC ... A61B 5/1036; A61B 5/1038; A61B 5/1122; A61B 5/1124; A61B 5/4005;
(Continued)

(56) References Cited

U.S. PATENT DOCUMENTS 3,861,790 A    1/1975  Tamura et al.
4,528,989 A    7/1985  Weinblatt
(Continued)

FOREIGN PATENT DOCUMENTS

EP    1297865 A1    4/2003
JP    H06165755 A    6/1994
(Continued)

OTHER PUBLICATIONS

Canadian Examiner's Report dated Jun. 29, 2017 in Canadian Patent Application No. 2,725,211, 6 pages.
(Continued)

*Primary Examiner* — Adam J Eiseman
(74) *Attorney, Agent, or Firm* — Shook, Hardy and Bacon L.L.P.

(57) ABSTRACT

The visual and cognitive skills of a subject may be tested and/or trained by providing a visual stimulus to a subject. More particularly, a subject may be tested and/or trained when under a stress condition to determine the effect of a stress condition, such as a physical stress or a cognitive stress, on the subject's visual and sensory skills. A response may be received from a subject via an input device, the appropriateness of which may depend upon the stimulus provided to the subject. Behavioral information and other data regarding the performance of a subject and the possible effect of the stress condition may be recorded. Scoring may be based upon the speed, accuracy, and other aspects of the performance of a subject.

6 Claims, 4 Drawing Sheets

(51) Int. Cl.
*A63B 24/00* (2006.01)
*G09B 7/00* (2006.01)
*A63B 21/06* (2006.01)
*A63B 22/02* (2006.01)
*A63B 22/06* (2006.01)
*A63B 23/04* (2006.01)
*A63B 23/12* (2006.01)
*G09B 7/02* (2006.01)
*G09B 19/00* (2006.01)

(52) U.S. Cl.
CPC ...... *A63B 22/0605* (2013.01); *A63B 22/0664* (2013.01); *A63B 23/0405* (2013.01); *A63B 23/1209* (2013.01); *A63B 24/0087* (2013.01); *A63B 71/06* (2013.01); *A63B 71/0619* (2013.01); *G09B 7/00* (2013.01); *G09B 7/02* (2013.01); *G09B 19/0038* (2013.01); *A63B 2022/0635* (2013.01); *A63B 2023/0411* (2013.01)

(58) Field of Classification Search
CPC ..... A61B 5/4023; A61B 5/4064; A61B 5/486; A63B 26/003
See application file for complete search history.

(56) References Cited

U.S. PATENT DOCUMENTS

| | | |
|---|---|---|
| 4,869,589 A | 9/1989 | Blair et al. |
| 5,050,982 A | 9/1991 | Meissner et al. |
| 5,088,810 A | 2/1992 | Galanter et al. |
| 5,478,239 A | 12/1995 | Fuerst et al. |
| 5,520,393 A | 5/1996 | Rickey et al. |
| 5,812,239 A | 9/1998 | Eger |
| 5,825,460 A | 10/1998 | Kohayakawa |
| 5,919,149 A | 7/1999 | Allum |
| 6,067,986 A | 5/2000 | Kluger et al. |
| 6,092,058 A | 7/2000 | Smyth |
| 6,206,702 B1 | 3/2001 | Hayden et al. |
| 6,261,239 B1 | 7/2001 | Abraham-Fuchs et al. |
| 6,267,733 B1 | 7/2001 | Peterson et al. |
| 6,364,845 B1 | 4/2002 | Duffy et al. |
| 6,371,931 B1 | 4/2002 | Guillen |
| 6,386,706 B1 | 5/2002 | McClure et al. |
| 6,430,997 B1 | 8/2002 | French et al. |
| 6,632,174 B1 | 10/2003 | Breznitz |
| 6,755,525 B2 | 6/2004 | Reichow et al. |
| 6,786,848 B2 | 9/2004 | Yamashita et al. |
| 6,811,258 B1 | 11/2004 | Grant |
| 6,893,127 B2 | 5/2005 | Reichow et al. |
| 7,073,208 B2 | 7/2006 | Penque, Jr. et al. |
| 7,326,060 B2 | 2/2008 | Seiller et al. |
| 7,849,115 B2 | 12/2010 | Reiner |
| 8,240,851 B2 | 8/2012 | Reichow et al. |
| 2002/0188219 A1 | 12/2002 | Suchard |
| 2003/0048280 A1 | 3/2003 | Russell |
| 2003/0078138 A1 | 4/2003 | Toyama |
| 2003/0120183 A1 | 6/2003 | Simmons |
| 2003/0211449 A1 | 11/2003 | Seiller et al. |
| 2004/0141152 A1 | 7/2004 | Marino |
| 2004/0167380 A1 | 8/2004 | Simon |
| 2005/0053904 A1 | 3/2005 | Shephard |
| 2005/0273017 A1 | 12/2005 | Gordon |
| 2006/0161218 A1 | 7/2006 | Danilov |
| 2006/0194178 A1 | 8/2006 | Goldstein |
| 2006/0195018 A1 | 8/2006 | Guillen |
| 2006/0244915 A1 | 11/2006 | Clemons et al. |
| 2006/0251334 A1 | 11/2006 | Oba et al. |
| 2006/0281061 A1 | 12/2006 | Hightower et al. |
| 2006/0287617 A1 | 12/2006 | Taub et al. |
| 2007/0000007 A1 | 1/2007 | MacDonald et al. |
| 2007/0013870 A1 | 1/2007 | Hara et al. |
| 2007/0027369 A1 | 2/2007 | Pagnacco et al. |
| 2007/0052674 A1 | 3/2007 | Culver |
| 2007/0179534 A1 | 8/2007 | Firlik et al. |
| 2007/0184953 A1 | 8/2007 | Luberski et al. |
| 2007/0197938 A1 | 8/2007 | Tyson et al. |
| 2007/0254270 A1 | 11/2007 | Hersh |
| 2008/0003553 A1 | 1/2008 | Stark et al. |
| 2008/0189173 A1 | 8/2008 | Bakar et al. |
| 2009/0093305 A1 | 4/2009 | Okamoto et al. |
| 2009/0129205 A1 | 5/2009 | Reichow et al. |
| 2009/0130640 A1 | 5/2009 | Hardy et al. |
| 2009/0150919 A1 | 6/2009 | Lee et al. |

FOREIGN PATENT DOCUMENTS

| | | |
|---|---|---|
| JP | H07299033 A | 11/1995 |
| JP | H10305016 A | 11/1998 |
| JP | H11225961 A | 8/1999 |
| JP | H11267101 A | 10/1999 |
| JP | H11318824 A | 11/1999 |
| JP | 2002219117 A | 8/2002 |
| JP | 2003102868 A | 4/2003 |
| JP | 2003126036 A | 5/2003 |
| JP | 2003126291 A | 5/2003 |
| JP | 2004135756 A | 5/2004 |
| JP | 2004329795 A | 11/2004 |
| WO | 9802083 A2 | 1/1998 |
| WO | 0017615 A2 | 3/2000 |
| WO | 02102469 A1 | 12/2002 |
| WO | 2004006747 A2 | 1/2004 |
| WO | 2006029048 A2 | 3/2006 |
| WO | 2006088415 A1 | 8/2006 |
| WO | 2007009990 A1 | 1/2007 |
| WO | 2008128183 A1 | 10/2008 |
| WO | 2008128192 A1 | 10/2008 |

OTHER PUBLICATIONS

European Notice of Allowance dated Jan. 24, 2017 in European Patent Application No. 08780526.3, 31 pages.
Office Action dated Sep. 1, 2017 in European Patent Application No. 09743649.7, 5 pages.
Non-Final Office Action dated Oct. 5, 2017 in U.S. Appl. No. 12/595,210, 14 pages.
Rouse, et al., "A Comparison Study of Dynamic Visual Acuity Between Athletes and Nonathletes", Journal of the American Optometric Association, Dec. 1988, pp. 946-950, vol. 59, No. 12, United States.
Coffey, et al., "Optometric Evaluation of the Elite Athlete," Problems in Optometry, Mar. 1990, pp. 32-59, vol. 2, No. 1, United States.
Reichow, et al., "Introduction to Behavioral Optometry", Sports Vision, 1993, 74 pages, Optometric Extension Program Foundation, United States.
Reichow, et al., "A Comparison of Contrast Sensitivity in Elite Athletes Versus a Normal Population", American Journal of Optometry and Physiological Optics, Dec. 15, 1986, vol. 63, No. 82, United States.
Farrow, et al, "An Investigation of the Effectiveness of Bolle's Competivision Sport-Glasses on Tennis Performance", Clinical and Experimental Optometry, Jul.-Aug. 2000, pp. 226-231, vol. 83, No. 4.
Herdman, et al., "Computerized Dynamic Visual Acuity Test in the Assessment of Vestibular Deficits", The American Journal of Otology, 1998, pp. 790-796, vol. 19, No. 6, United States.
Tian, et al., "Dynamic Visual Acuity During Transient and Sinusoidal Yaw Rotation in Normal Ulilaterally Vestibulopathic Humans", Experimental Brain Research, Feb. 8, 2001, pp. 12-25, vol. 137, Springer-Verlag, United States.
Coffey, et al., "Visual Performance Enhancement in Sports Optometry", Sports Vision 1995, pp. 158-177, Butterworth-Heinermann, United States.
Ferreira, "An Overview of Research in Sports Vision: its History and an Optometric Perspective", The South African Optometrist, Dec. 2003, pp. 142-149, vol. 62, No. 4, Auckland Park, South Africa.

(56) References Cited

OTHER PUBLICATIONS

Koenig, "Practicing Perception: Eyes Can Be Trained to be More Effective", USA Today Baseball Weekly, 1996, 3 pages, United States.

Cardall, "Contact Lenses in Sport: a General Overview", Optician, Jan. 13, 2006, pp. 22-25, vol. 231, No. 6034, United States.

Reichow, et al., "Ultraviolet and Short Wavelength Visible Light Exposure: Why Ultraviolet Protection Alone is Not Adequate", Journal of Long-Term Effects of Medical Implants, 2006, pp. 315-325, vol. 16, No. 4, Begell House, Inc., United States.

A. Ludeke, et al., "The difference in visual skills between professional versus non-professional rugby players'" The South African Optometrist, Dec. 1, 2003 pp. 150-158, XP055044423.

Martijn Ltm Muller: "Attentional components of postural control" Dissertation, 2007, XP055044427, Saline MI (USA) Retrieved from the Internet: URL: http://dare.uva.n/document/48212 [retrieved on Nov. 15, 2012].

Official Guidebook by Nintendo, "Rhythm Heaven", Shogajujan, Inc., Nov. 1, 2006, pp. 4, 5, 14, 15, 26, 27, 28, 29.

Kazutaka Toyoomi, Nintendo has improved "Visual Ability" through a simple training. DS software: "DS Visual Ability Training for Improving Ability to See through Actual Practice" GAME Watch, May 18, 2007, http://game.watch.impress.co.jp/docs/20070518/meji.htm.

Shigenori Agura, "Sports Vision", Science for Children, October issue, Sep. 17, 2002, vol. 65 (10), pp. 10-18.

Kathryn W. O'Connor et al.: "Postural adaptations to repeated optic flow stimulation in older adults",Gait & Posture, vol. 28, No. 3 Mar. 10, 2008, pp. 385-391. Retrieved from the Internet Sep. 9, 2014: URL:http://www.ncbi.nlm.nih .gov/pmc/articles/PMC2605319/.

Mark S. Redform et al.: "Attention influences sensory integration for postural control in older adults",Gait & Posture, vol. 14, No. 3Dec. 1, 2001, pp. 211-216.

Final Office Action dated Feb. 8, 2017 in U.S. Appl. No. 12/995,210, 14 pages.

Canadian Office Action dated Mar. 10, 2017 in Canadian Patent Application No. 2767654, 6 pages.

VISION AND COGNITION TESTING AND/OR TRAINING UNDER STRESS CONDITIONS

CROSS-REFERENCE TO RELATED APPLICATIONS

This application is a divisional of co-pending U.S. patent application Ser. No. 12/117,315, filed May. 8, 200, and titled "Vision and Cognition Testing and/or Training Under Stress Conditions," the entire contents of which are incorporated herein by reference in their entirety.

STATEMENT REGARDING FEDERALLY SPONSORED RESEARCH OR DEVELOPMENT

Not applicable.

TECHNICAL FIELD

The present invention relates to the testing and training of vision and cognitive function. More particularly, the present invention relates to training and testing visual and/or cognitive processing under stress conditions.

BACKGROUND

One skilled in the art of vision evaluation will be aware of a large number of vision tests that may be performed upon a subject to determine the strengths and weaknesses of an individual's visual abilities. Typically, such tests are applied to determine whether an individual may benefit from some form of vision correction and/or training and, if so, what type and degree of vision correction and/or training may be desirable. Further, numerous activities, particularly competitive athletics, place particularized demands upon the visual abilities of an individual, and awareness of any effect caused by such demands on visual or cognitive abilities is also desirable. However, an individual's visual ability is not always static, as it may be affected by physiological changes such as those accompanying physical or cognitive stress such as for example increased blood pressure.

SUMMARY

Systems and methods in accordance with the present invention test or train the vision and/or cognition abilities of a subject under stress conditions by subjecting a subject to a stress condition, providing a visual stimulus, and receiving a response from a subject. Stress conditions may include physical stress and/or cognitive stress, such as an aerobic activity or an anaerobic activity. Stimulus presented to a subject may be, for example, a visual stimulus presented on a display device. A response may be received from a subject through an input device.

In another embodiment in accordance with the present invention, a system is provided that may comprise a display device, a stress-inducing device that subjects an individual to a stress condition, and a test unit coupled to the display device. A display device in this system may be configured to display a visual stimulus to a test subject. Such a system may also include an input device configured to receive a response from the test subject.

In yet another embodiment in accordance with the present invention, a method for visual and cognitive testing or training is provided. The method may comprise administering a first test to a subject to produce test results, where the test may be a visual test and/or a cognitive test; recording the test results from this first test; subjecting the test subject to a stress condition; administering a second test to the test subject to produce test results, where the test may be a visual test and/or a cognitive test; recording the second test results; and determining the difference between the first test results and the second test results.

BRIEF DESCRIPTION OF THE DRAWINGS

The present invention is described in detail below with reference to the attached drawing figures, wherein.

DETAILED DESCRIPTION

Figure 1:
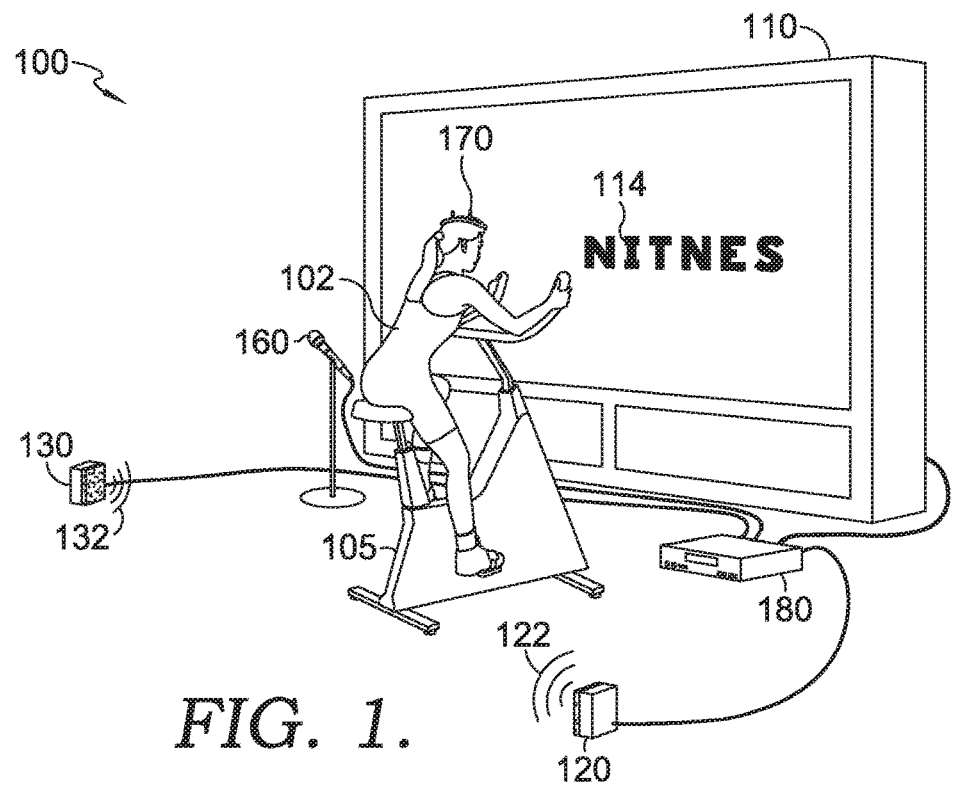
FIG. 1 illustrates a system in accordance with the present invention.

Referring now to the figures, FIG. 1 illustrates a testing/training system 100 in accordance with the present invention. It will be understood by one of ordinary skill in the art that the systems and methods described herein may be applicable for both testing and training purposes. System 100 may be used to test/train subject 102.

In FIG. 1, test subject 102 may be subjected to stress conditions by device 105. Device 105 may include any device that may place stress, such as, for example, a physical stress, on test subject 102. Exposing a test subject to stress conditions while testing the subject's visual and cognitive abilities may show the affect of such stress on the subject's abilities. It is important, particularly in athletic competition, to maintain one's vision and cognitive abilities; however, these abilities may deteriorate as the stress of the activity, competition, or game continues. Testing this decline in visual and/or cognitive abilities may help to identify this issue for an individual, and subsequently the individual may train to better maintain their visual and/or cognitive abilities despite such stress. One skilled in the art will appreciate that test subject 102 may undergo more than one round of testing. One skilled in the art will further appreciate that more than one test subject may undergo testing simultaneously. One skilled in the art will also appreciate that systems in accordance with the present invention, such as system 100, may be used for training purposes to improve the visual and/or cognitive abilities of an individual under stress conditions.

Although device 105 in FIG. 1 provides a stress condition in the form of aerobic activity, physical stress may include both aerobic and anaerobic activity. Examples of aerobic activity include any activity that raises the aerobic level of the subject, including running, cycling, elliptical training, etc. Anaerobic activities may include any type of strength training or weight training that may impose a physical stress upon test subject 102, including bench pressing, squatting, etc.

In accordance with the present invention, visual and/or cognitive tests may be performed on an individual. Visual tests may include any visually demanding activity, such as having a subject read from an eye chart Likewise, cognitive tests may include any cognitively demanding activity. Examples of such activities may include various arithmetic, verbal, directional tests, and the like. One of ordinary skill in the art will appreciate that the degree of difficulty of these activities may vary based on the individual's level and the particularized activity of the individual. The difficulty of such activities may also vary during the course of the testing. For example, the tests may begin at an easy level, and with each round of testing, may increase in difficulty.

In performing the visual and/or cognitive testing, the displayed stimulus (e.g., indicia 114) may possess traits that may be perceived by a user. For example, the stimulus may possess a particular color, or may be a particular character, such as a digit or letter as shown by indicia 114. Alternatively, a displayed stimulus may possess traits such as orientation. For example, a stimulus may comprise an arrow or a Landolt C pointing up, down, left or right, and subject 102 may provide a response (e.g., by depressing a button, moving a joystick, providing voice recognition, shifting weight, etc.), corresponding to the direction of the displayed arrow.

In accordance with the present invention, methods subjecting a subject to a stress condition may occur in various ways. By way of example, without limitation, an individual may be subjected to a stress condition for a specific duration of time, the stress condition may terminate, and then subsequently the individual may be subjected to visual and/or cognitive testing. To determine the effect of a stress condition on an individual, vision and/or cognitive testing may occur prior to subjecting the individual to the stress condition to provide baseline data with which to compare later vision and/or cognitive test results.

The duration of the physical activity or stress may vary and may be repeated at longer or shorter intervals. Further, the intensity of the activity may vary. For example, if a treadmill was used as device 105, the speed or incline of the treadmill might increase with each round of testing, or if the stress was provided by weight training, more weight might be added for the individual to lift. One skilled in the art will appreciate that the intensity may also increase or decrease within each round. One skilled in the art will further appreciate that the determination of the type, duration, and intensity of the stress condition may be determined based on the particularized needs of the athlete.

In another embodiment of the present invention, an individual may be subjected to both visual and/or cognitive testing and a stress condition simultaneously. Visual and/or cognitive testing may also occur prior to subjecting the individual to the stress condition in order to have baseline data for comparison purposes. This embodiment may be used for athletes who participate in sports that require the athlete to be in a continuous stress condition, such as soccer, basketball, and the like.

Referring to FIG. 1, display device 110 may be positioned so that subject 102 may view display device 110. Display device 110 may be any type of computer or television monitor, including cathode ray tub, liquid crystal display, plasma screen, or any other display type, or may comprise a screen upon which images are projected, either from the from or from the rear. Further, display device 110 may be combined with device 105 in system 100, or, alternatively, display device 110 and device 105 may be separate devices. While a single display device 110 is illustrated in FIG. 1, multiple display devices may also be used.

Display device 110 may provide a stimulus, such as visual indicia 114. As illustrated in FIG. 1, visual indicia 114 provides an example of an indicia that may be used in accordance with the present invention. As illustrated in FIG. 1, indicia 114 is a string of letters that spells "NITNES." For this example, subject 102 may be tested cognitively by requiring her to organize the letters to spell a word, here "TENNIS." However, one of ordinary skill in the art will appreciate that any other type of indicia may be used in accordance with the present invention. For example, another appropriate indicia for use in the present invention may be a Landolt C.

In responding to the visual stimulus displayed to test subject 102, test subject 102 may provide a response via an input device. An input device may include any device capable of receiving input from a user, such as a touch-sensitive display device, an audio device, a motor input device, etc. By way of example, without limitation, display device 110 may be touch-sensitive, thereby permitting it to receive inputs as well. A touch-sensitive display device 110 may comprise a monitor, projection screen, or any other type of display device without touch-sensitivity operatively coupled to a touch sensitive layer that permits both the display of visual stimuli and the receipt of touch inputs. For example, a touch-sensitive and substantially transparent film may be applied over a non-touch-sensitive monitor. By way of further example, a touch-sensitive board may be used in conjunction with a projector as a touch-sensitive display 110. These and other possibilities for use as a touch-sensitive display device will be understood to those of ordinary skill in the art.

Figure 3:
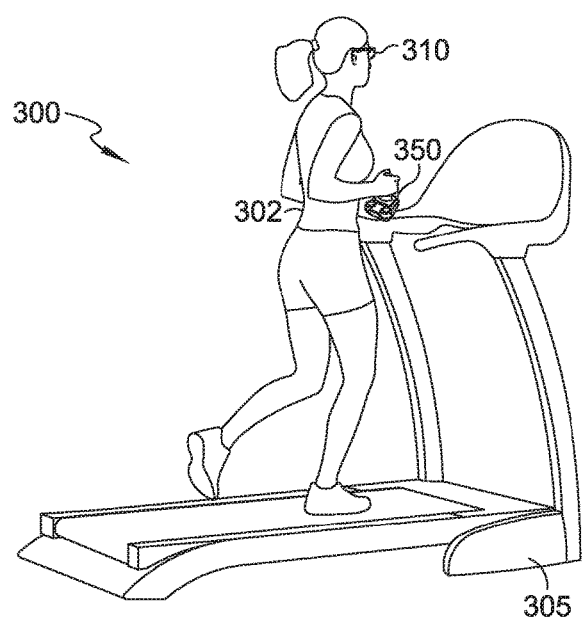
FIG. 3 illustrates a further system in accordance with the present invention.

Subject 102 may further provide responses using a motor input device (e.g., device 350 in FIG. 3). Motor input device may be any device, such as a joystick or keypad, capable of receiving manual input from subject 102, and may also be any device capable of receiving input from any other type of physical action by subject 102, such as foot actuated pedals or buttons. Examples of appropriate devices for use as input device 150 include keyboards or keypads, buttons, joysticks, switches, pedals, or any other device capable of receiving an active input from subject 102. Further examples of input devices are discussed below.

Still referring to FIG. 1, input devices may also comprise a microphone 160 that receives input from subject 102. Microphone 160 may, for example, be used in conjunction with voice recognition software to receive vocal responses from subject 102. In the example illustrated in FIG. 1, microphone may be used in conjunction with voice recognition software operating on testing unit 180 to recognize the word "TENNIS" when spoken by subject 102. Examples of other types of vocal responses include the identity of a series of digits displayed on display device 110, the orientation of an indicia displayed on display device 110, the color of an indicia displayed on display device 110, the region of display device 110 on which an indicia is displayed, or any other type of verbal information.

Further referring to FIG. 1, system 100 may include head and/or eye monitor 170. Head and/or eye monitor 170 may measure the movement of the head and/or eyes of subject 102 during testing/training. In a further example, input may be received by capturing the gestures of the subject's body movement. Other equipment (not illustrated) may measure data such as a subject's brain activity, blood pressure, heart rate, perspiration, or other biological and/or medical data. By way of example, without limitation, the brain activity of a subject may be used as an input device by utilizing an EEG to capture brain activity, particularly brain activity that is linked to the subject's vision.

Still referring to FIG. 1, system 100 may include an audio speaker 120 that may emit a sound 122. Audio stimuli may be used in conjunction with the present invention. For example, methods in accordance with the present invention may use sound in conjunction with vision and/or cognition testing/training as part of preparing a subject to perform in a competitive environment where there may be distractions due to crowd noise or other sounds. Further, sound may be used as a stimuli requiring a particular response from a subject. Potentially, a subject may be required to respond in a given way to a particular combination of stimuli, such as responding to a visual stimuli only when paired with a particular sound. Multiple speakers may be used beyond the audio speaker 120 shown in FIG. 1, which may permit a subject to test/train to differentiate sounds based upon their direction of origin.

Test unit 180 may coordinate the stimulus or stimuli provided by various output devices in system 100 and collect and retain input data from the responses of subject 102 and any additional data, such as balance, eye movement, head movement data, and biological/medical data received from subject 102. Test unit 180 may further provide scoring functionality to provide a measure of the accuracy, speed, and other performance criteria of subject 102. Test unit 180 may further control the testing process so that the presentation of a stimulus to subject 102 increases in speed or difficulty as subject 102 progresses through testing/training.

Figure 2:
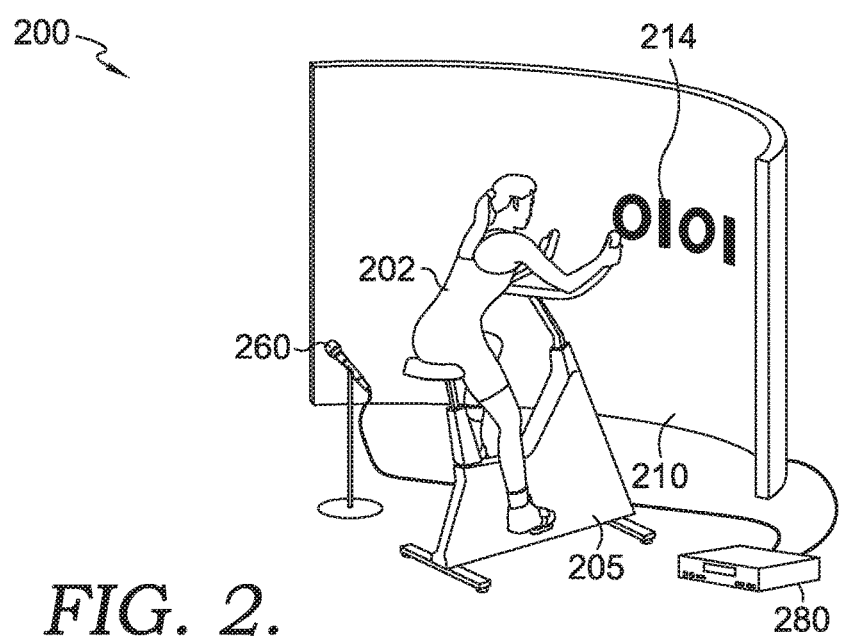
FIG. 2 illustrates a further system in accordance with the present invention.

FIGS. 2 and 3 provide further examples of tests that may be used to test an individual's visual and/or cognitive abilities. With each example, it is to be understood that the individual may be subjected to a stress condition, as described above. One skilled in the art will appreciate that these figures merely illustrate examples of testing that may be used in conjunction with the stress condition.

Referring now to FIG. 2, a portion of a second example system 200 in accordance with the present invention is illustrated. System 200 utilizes an arcuate display device 210 oriented partially around subject 202. A device, such as device 205, may be used to create a stress condition for subject 202. Arcuate display device 210 may display an indicia 214. System 200 may further include a variety of additional components, such as those illustrated in FIG. 1. For example, in FIG. 2, subject 202 may respond via an audio input, such as microphone 260. Arcuate display device 210 may be useful to both provide subject 202 a more immersive visual experience, to test portions of the field of vision of subject 202 not easily tested/trained using a single flat display device.

Referring now to FIG. 3, a portion of a system 300 utilizing display goggles 310 are illustrated. Display goggles 310 may present visual imagery to subject 302 without the need for a larger display device. In FIG. 3, device 305 provides a stress condition for subject 302. System 300 may include an input device 350 that may receive responses from subject 302. Input device 350 may be any of the input devices described above with regard to input device 150 in FIG. 1, or may alternatively be a microphone. Input device 350 may be, for example, a motion sensitive glove or other device worn by subject 302 to measure the movement of the hand of subject 302 in response to visual stimuli displayed using goggles 310 to measure the eye-hand coordination of subject 302. It should further be appreciated that goggles 310 may include integrally therein head and/or eye movement monitors, or other biological/medical monitors.

Figure 4:
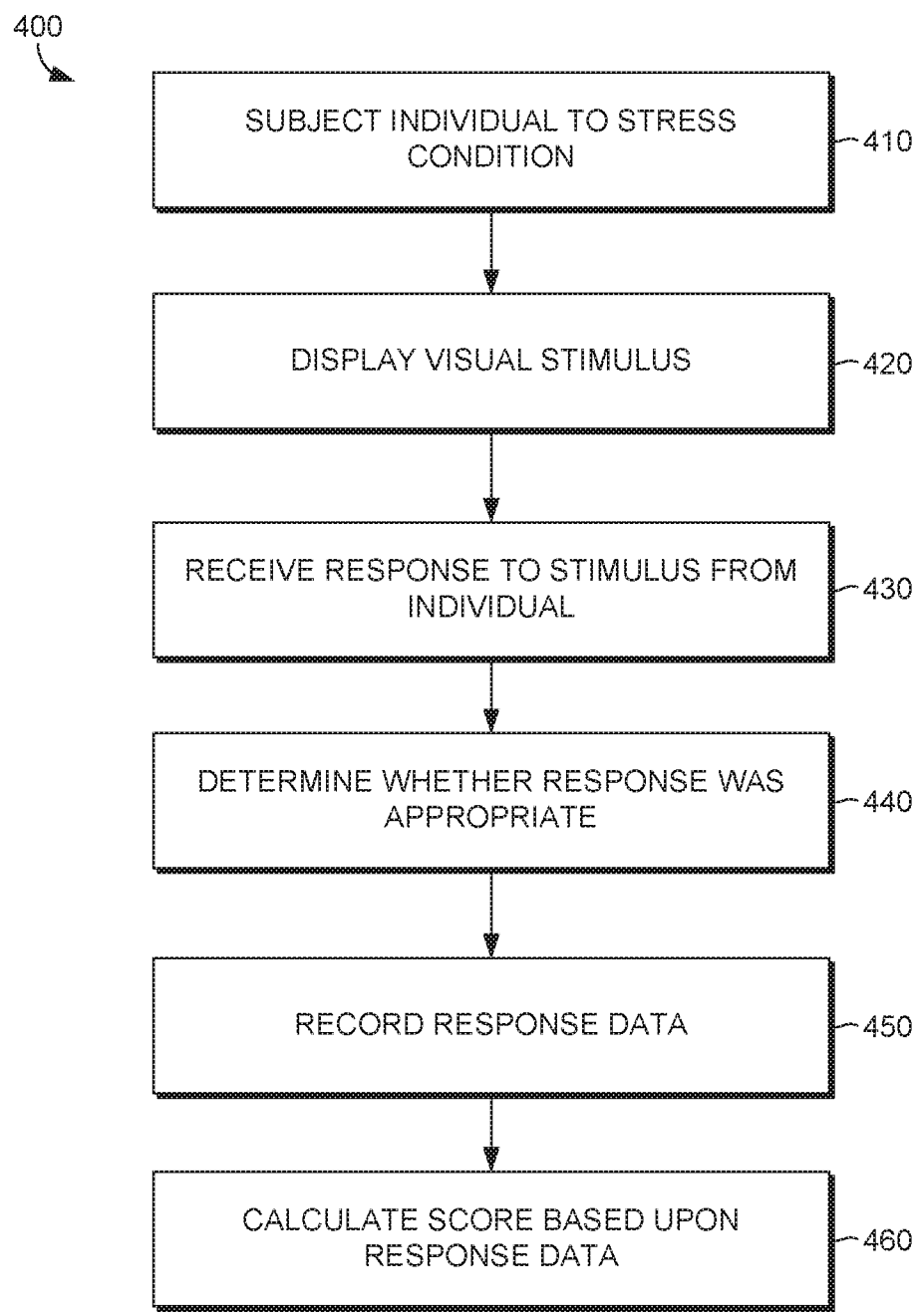
FIG. 4 illustrates a method in accordance with the present invention.

Referring now to FIG. 4, a method 400 of testing/training a subject's visual and/or cognitive function is illustrated. In step 410, an individual is subjected to a stress condition. In step 420 a visual stimulus, such as an indicia, is displayed on a display device. At step 440, an input is received. An input received from an individual may comprise a touch input, an audio input, or a motor input device, as described above. In step 440, it is determined whether the response to the indicia was appropriate. For example, an appropriate response might be to touch a displayed visual stimulus, to ignore a displayed visual stimulus, to verbally respond to a displayed visual stimulus (for example, by reciting identifying characteristics of the stimulus), or to provide a response using a motor input device. In step 450, data regarding the response and whether the response was appropriate is recorded on a digital media. In step 460, a score may be calculated based upon the response. One skilled in the art will appreciate that the score calculated in step 460 may be based upon further information, such as a subject's head and/or eye movement, biological/medical data or other information collected from the subject.

Figure 5:
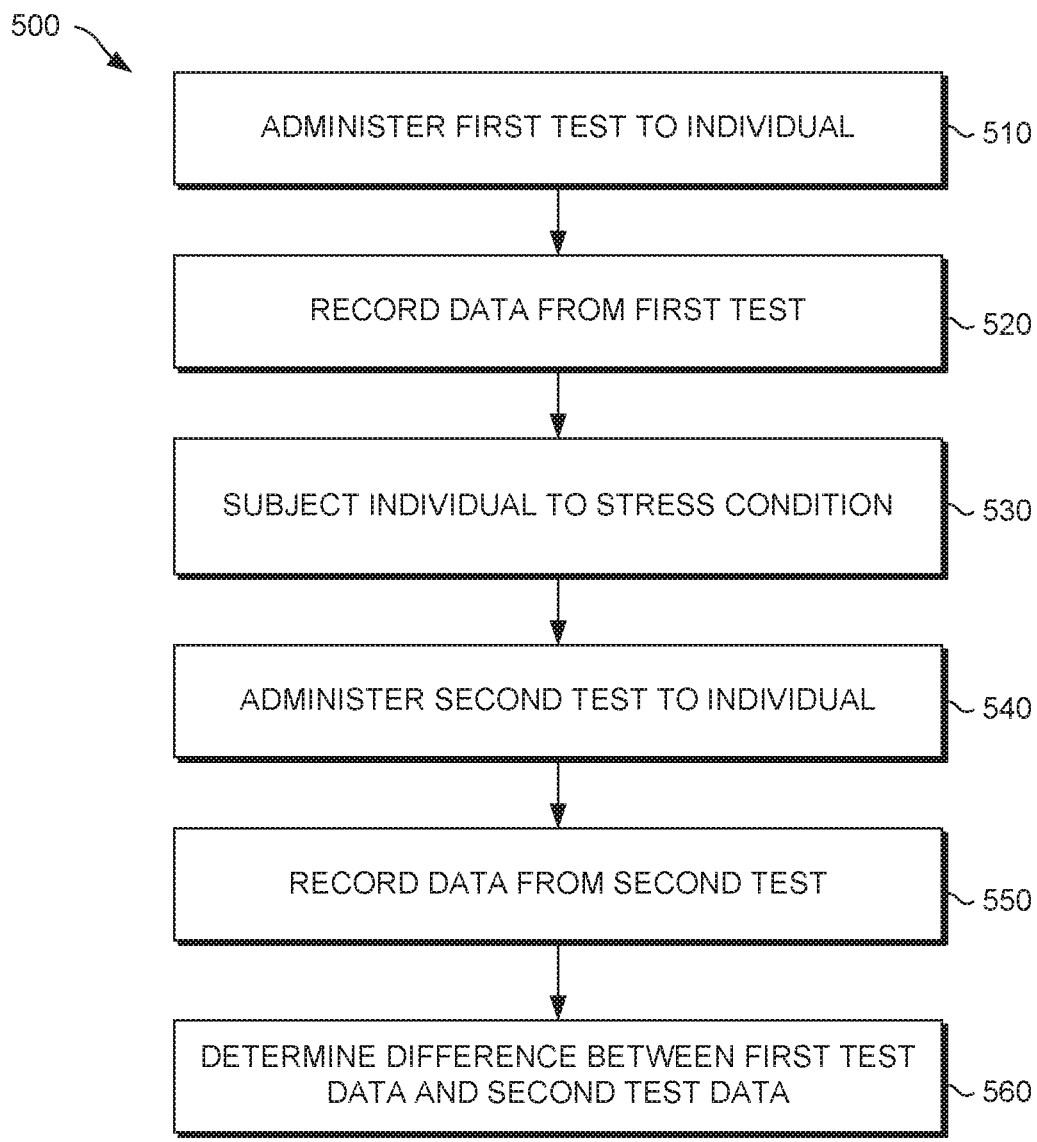
FIG. 5 illustrates a further method in accordance with the present invention.

Referring now to FIG. 5, a further method 500 of testing/training a subject's visual and cognitive abilities is illustrated. In step 510 a visual and/or cognitive test is administered. Such a test may include a visual stimulus, such as, for example, a visual indicia. As described above, examples of tests that may be performed at step 510 include visual, arithmetic, verbal, directional tests, and the like. For example, an arithmetic problem might be displayed for the subject to solve, such as 2+3, or, as illustrated in FIG. 1, the letters of a word might be jumbled, requiring the subject to correctly spell the word. For a visual test, the subject may be required to read, for example, from a standard eye chart. The subject's cognitive and visual abilities might be tested with a directional test, where an arrow or other indicia (such as a Landolt C) is displayed, and the subject is required to respond with the direction of the arrow via an input device. One skilled in the art will understand and appreciate that the tests administered in step 510 may be configured as necessary.

In step 520, the results received from the tests administered in step 510 are recorded. In step 530, a test subject may be subjected to a stress condition. In step 540, a visual and/or cognitive test is administered. Stress conditions, as described above, may include any aerobic or anaerobic activity. The test administered in step 540 may be identical to the test administered in step 510, or alternatively, the test administered in step 540 may differ from the test administered in step 510. While, in method 500, step 530 is illustrated as occurring before step 540, it will be appreciated that steps 530 and 540 may occur simultaneously. In step 550, the results of the test administered in step 540 are recorded. In step 560, the difference between the results recorded in step 520 and step 550 is calculated. This difference may indicate the effect of the stress condition on the subject's visual and/or cognitive abilities.

The systems and methods described herein may be utilized to test and/or train a variety of visual and cognitive skills. The types of physical activities used to stress an individual are not limited to those described herein, but rather may utilize any type of activity capable of providing stress to a subject. Further, the types of output devices used to provide stimuli to a subject are not limited to those described herein, but rather may utilize any type of device capable of providing stimuli to a subject. The systems and methods described herein are further not limited to any particular scoring algorithm or criteria, and the scoring algorithms and criteria may be adjusted for different subjects or as individual subjects progress in skill Similarly, the number and types of stimuli provided to a subject and response received by a subject are not limited to those described herein, and multiple types of stimuli and multiple types of responses may be provided and received in any individual testing/training session.

What is claimed is:

1. A system for improving athletic performance of a test subject, the system comprising:
   a first apparatus, comprising:
      a test unit,
      at least one display device, and
      at least one monitor for monitoring at least one of eye movement and head movement of the test subject; and
   a second apparatus comprising a stress-inducing device configured to provide a stress to the test subject,
      wherein the first apparatus is configured to provide a test to the test subject by:
         displaying a visual stimulus to the test subject on the at least one display device;
         determining a correct response to the visual stimulus;
         receiving a response from the test subject;
         capturing at least one of head movement and eye movement of the test subject using the at least one monitor;
         determining if the response is the correct response; and
         calculating a score based on the response being correct or incorrect and a degree of head or eye movement of the test subject captured by the at least one monitor,
      wherein the system is configured so the first apparatus can provide the test to the test subject at the same time as the second apparatus provides the stress to the test subject.

2. The system of claim 1, wherein the test unit is communicatively coupled to the at least one display device and the at least one monitor.

3. The system of claim 1, further comprising an input device communicatively coupled to the test unit and configured to receive an input from the test subject as the response.

4. The system of claim 3, wherein the at least one display device and the input device are the same.

5. The system of claim 1, wherein the stress-inducing device is a device for one of running, cycling, and elliptical training.

6. The system of claim 1, wherein the stress-inducing device is a speaker and the stress is a sound emitted from the speaker.

* * * * *

UNITED STATES PATENT AND TRADEMARK OFFICE
CERTIFICATE OF CORRECTION

PATENT NO. : 10,155,148 B2
APPLICATION NO. : 15/389516
DATED : December 18, 2018
INVENTOR(S) : Alan W. Reichow and Herb Yoo Page 1 of 1

It is certified that error appears in the above-identified patent and that said Letters Patent is hereby corrected as shown below:

On the Title Page

Item (56) Other Publications, Page 3, Column 1, Line 15: Please remove "//dare.uva.n/" and replace with --//dare.uva.n./--.

In the Specification

Column 1, Line 8: Please remove "May. 8,200," and replace with --May 8, 2008,--.
Column 2, Line 64: Please remove "chart" and replace with --chart.--.
Column 3, Line 54: Please remove "tub," and replace with --tube,--.
Column 6, Line 62: Please remove "skill" and replace with --skill.--.

Signed and Sealed this
Ninth Day of April, 2019

Andrei Iancu
*Director of the United States Patent and Trademark Office*